United States Patent
Deshpande et al.

(10) Patent No.: US 6,903,211 B2
(45) Date of Patent: Jun. 7, 2005

(54) PROCESS FOR THE PREPARATION OF 3-PROPENYL CEPHALOSPORIN DMF SOLVATE

(75) Inventors: Pandurang Balwant Deshpande, Chennai (IN); Bhausaheb Pandharinath Khadangale, Chennai (IN); Kumar Gurusamy, Chennai (IN); Ramesh Athmaram Konda, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 55 days.

(21) Appl. No.: 10/315,010

(22) Filed: Dec. 10, 2002

(65) Prior Publication Data

US 2004/0087786 A1 May 6, 2004

(30) Foreign Application Priority Data

Oct. 30, 2002 (IN) .................... 800/MAS/2002

(51) Int. Cl.[7] .......................................... C07D 510/22
(52) U.S. Cl. ...................................................... 540/215
(58) Field of Search .......................................... 540/215

(56) References Cited

U.S. PATENT DOCUMENTS

| | | | |
|---|---|---|---|
| 4,694,079 A | * | 9/1987 | Crast, Jr. .................... 540/215 |
| 4,699,979 A | * | 10/1987 | Hoshi et al. ................. 540/215 |
| 4,727,070 A | * | 2/1988 | Kaplan et al. ............... 540/215 |
| 5,922,861 A | * | 7/1999 | De Vroom et al. .......... 540/304 |

* cited by examiner

Primary Examiner—Mark L. Berch
(74) Attorney, Agent, or Firm—Oliff & Berridge, PLC

(57) ABSTRACT

The present invention relates to an improved process for the preparation of cefprozil DMF solvate of formula (I),

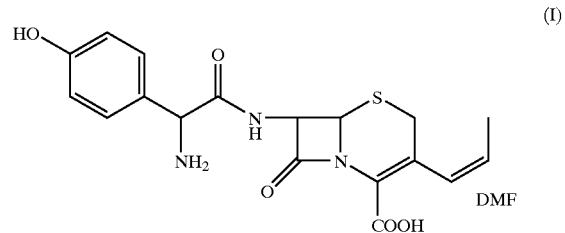

(I)

which is useful for the preparation of cefprozil, comprising:
 i) reacting a compound of formula (VIII) with acetaldehyde to produce a compound of formula (IX),
 ii) deesterifying the carboxy protecting group of the compound of formula (IX) using an acid to yield a compound of formula (X),
 iii) converting the compound of formula (X) to a compound of formula (XI),
 iv) neutralizing the compound of formula (XI) followed by enzymatic hydrolysis to produce an APCA of formula (V),
 v) silylating the APCA using a mixture of trimethylsilylchloride and hexamethyldisilazane to produce silylated APCA of formula (XII), and
 vi) condensing the silylated APCA with a mixed anhydride to produce the DMF solvate compound of formula (I).

12 Claims, No Drawings

PROCESS FOR THE PREPARATION OF 3-PROPENYL CEPHALOSPORIN DMF SOLVATE

FIELD OF THE INVENTION

The present invention relates to an improved process for the preparation of 3-propenyl cephalosporin DMF solvate. More particularly, the present invention relates to an improved process for the preparation of cefprozil DMF solvate of the formula (I).

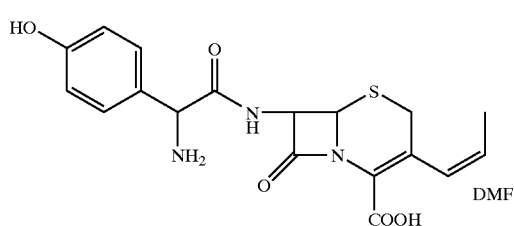

(I)

The 3-propenyl cephalosporin DMF solvate of the formula (I) is useful for the preparation of cefprozil of the formula (XIV).

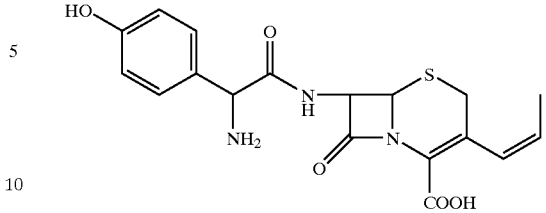

(XIV)

BACKGROUND OF THE INVENTION

Cefprozil is chemically known as (6R,7R)-7-[2-amino-2-(4-hydroxyphenyl)acetamido]-3-[(Z)-propenyl]-3-cephem-4-carboxylic acid. It is an orally effective cephalosporin antibiotic having a broad spectrum of antibacterial activity against both gram positive and gram-negative organisms and is disclosed in U.S. Pat. No. 4,520,022.

U.S. Pat. No. 4,694,079 discloses a process for the preparation of DMF solvate of cefprozil as shown in scheme I below:

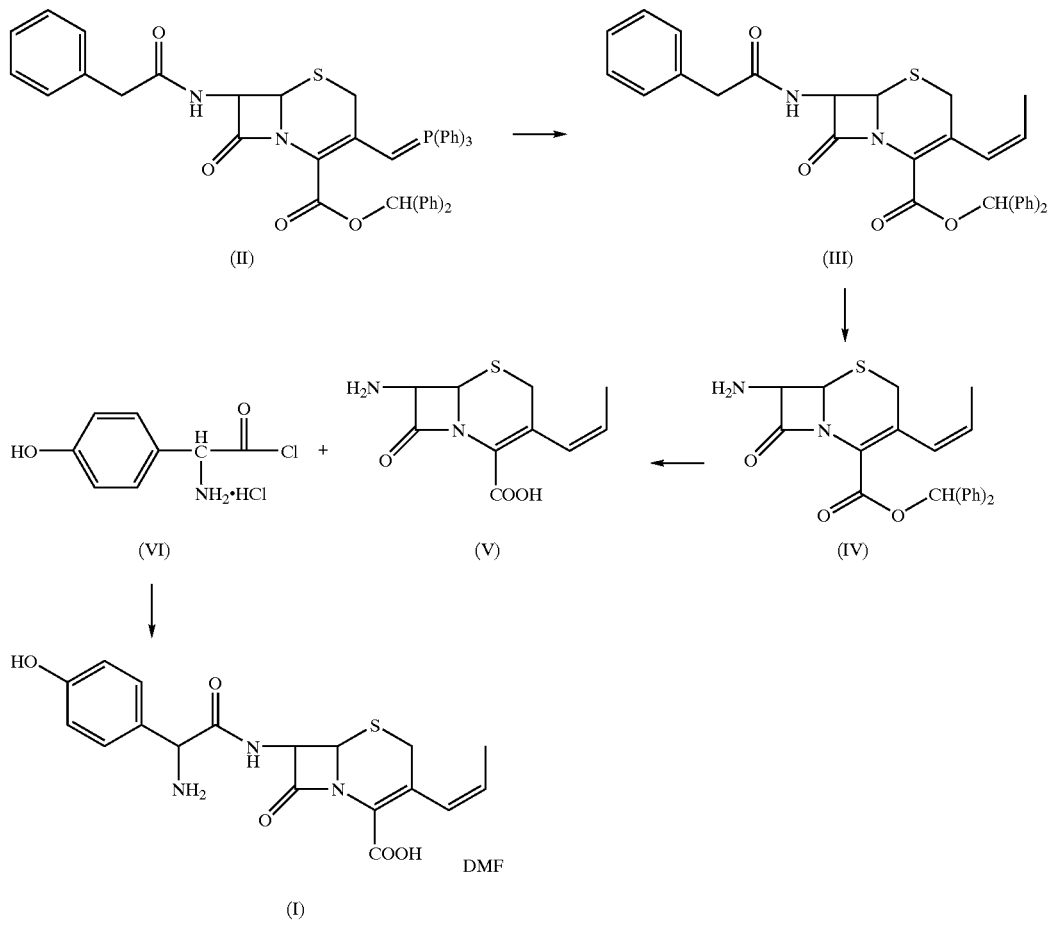

The yield of the cefprozil obtained from this process is only 65%.

Scheme-1

U.S. Pat. No. 5,608,055 discloses a process for the production of 7-α-aminoacyl-cephalosporin by acylating 7-amino-3-cephem-4-carboxylic acid or a derivative thereof in a halogen-free solvent. The yields in the process are very low.

U.S. Pat. Nos. 5,869,648 and 6,136,967 discloses a process for the preparation of cefprozil comprising:

i) preparing a (Z)-isomer enriched 7-amino-3-(1-propen-1-yl)-3-cephem-4-carboxylic acid (APCA) by depleting 7-amino-3-{(E)-1-propen-1-yl}-3cephem-4-carboxylic acid in a Z/E mixture of 7-amino-3-(1-propen-1-yl)-3-cephem-4-carboxylic acid a) by forming the hydrochloride of APCA in a solvent or solvent mixture and recovering the enriched Z-isomer and optionally converting the hydrochloride into the free acid with reduced E amount by adjusting the pH, or forming a salt of APCA and converting the salt to APCA with reduced E amount or subjecting the solution of APCA to adsorption chromatography, and ii) acylating the (Z)-isomer enriched 7-amino-3-(1-propen-1-yl)-3-cephem-4-carboxylic acid in free acid or salt form obtained in step (i) at the amine group in position 7 of the ring system to obtain cefprozil. This patent discloses different salts of APCA and the preparation of cefprozil using these salts. The salts discloses are lithium, sodium, potassium, ammonium, cyclohexyl amine, dicyclohexyl amine. The Z/E ratio of the product before the chromatography or further purification is 85/15. After purification the Z-isomer ratio is increased to greater than 90%.

One of the processes described uses adsorption chromatography for the separation of isomers, which cannot be done on an industrial scale very easily. The other processes use further crystallization for getting enriched (Z) isomer, which involves use of high volumes of solvent.

With the process described in the prior art, it is not possible to obtain the high isomeric purity. The product obtained by all the processes contains very high content of (E) isomer. We, therefore, focussed our research to identify a process, which gives product with high isomeric purity.

OBJECTIVE OF THE INVENTION

The main objective of the present invention is to provide an improved process for the preparation of 3-propenyl cephalosporin DMF solvate of the formula (I).

Another objective of the present invention is to provide a stable process for the preparation of 3-propenyl cephalosporin DMF solvate of the formula (I) with (Z)-isomer enrichment.

Yet another objective of the present invention is to provide a stable process for the preparation of 3-propenyl cephalosporin DMF solvate of the formula (I) using halogenated solvents in high purity and yield.

Yet another objective of the present invention is to provide a stable process for the preparation of 3-propenyl cephalosporin DMF solvate of the formula (I), which avoids the use of adsorption chromatography or recrystallization methods in any stage of the process and easy to operate on industrial scale.

Yet another objective of the present invention is to provide a process for the preparation of cefprozil using 3-propenyl cephalosporin DMF solvate of the formula (I).

SUMMARY OF THE INVENTION

Accordingly, the present invention provides an improved process for the preparation of cefprozil DMF solvate of the formula (I)

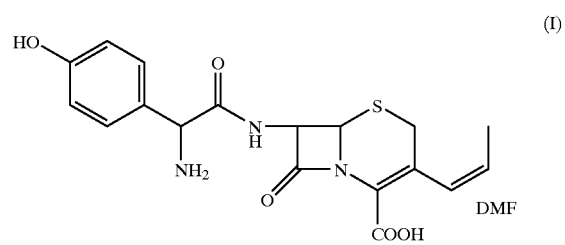

comprising the steps of:

i) converting the compound of formula (VII) wherein $R_1$ represents carboxy protecting group to a compound of the formula (VIII) using triphenylphosphine in the presence of solvent and alkali iodide, ii) reacting the compound of formula (VIII) with acetaldehyde using lithium chloride in the presence of solvent at a temperature in the range of −10° C. to 30° C. to produce a compound of formula (IX) wherein $R_1$ is as defined above, iii) deesterifying the carboxy protecting group of compound of the formula (IX) using an acid in the presence of solvent at a temperature in the range of 10° C. to 50° C. to yield compound of formula (X), iv) converting the compound of formula (X) to compound of formula (XI) wherein $M^+$ represents a counter ion which forms a salt in the presence of a base and solvent, v) neutralizing the compound of formula (XI) followed by enzymatic hydrolysis to produce APCA of formula (V), using conventional methods, vi) silylating the APCA of formula (V) using a mixture of trimethyl silylchloride and hexamethyl disilazane in the presence of a halogenated solvent to produce silylated APCA of formula (XII) and vii) condensing the silylated derivative of APCA of the formula (XII) with the mixed anhydride of the formula (XIII) wherein $R_2$ represents alkyl, phenyl, benzyl or cycloalkyl and $R_3$ represents methyl, ethyl or isopropyl, in the presence of DMF, a halogenated solvent and a base at a temperature in the range of −50° C. to 10° C. to produce cefprozil DMF solvate of formula (I).

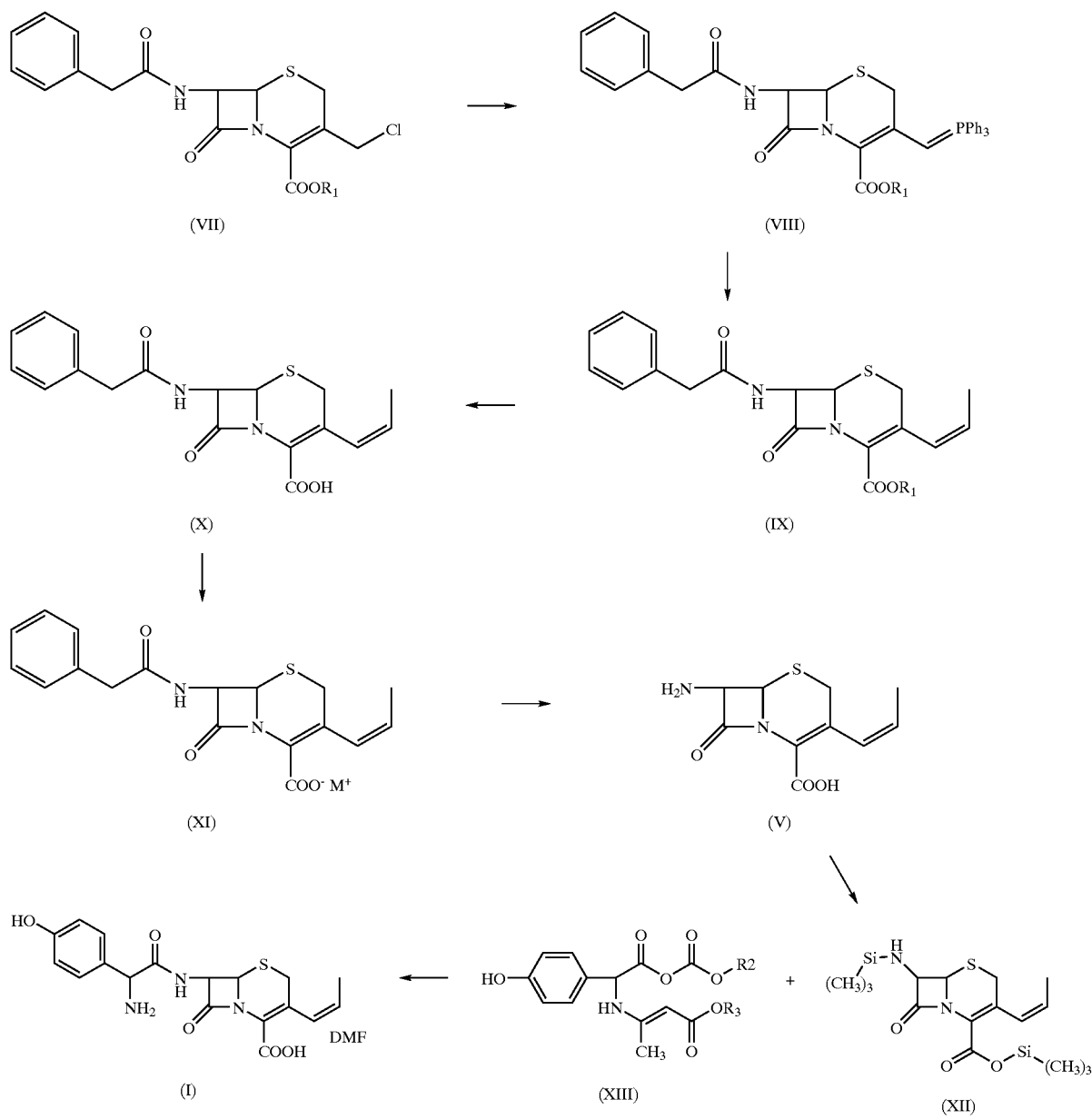

Scheme-2

DETAILED DESCRIPTION OF THE INVENTION

In an embodiment of the present invention, the carboxy protecting group represented by $R^1$ is selected from ($C_1$–$C_6$) alkyl group such as methyl, ethyl, propyl, isopropyl, t-butyl and the like; p-methoxybenzyl, p-nitrobenzyl, o-chlorobenzyl, diphenylmethyl and the like.

In yet another embodiment of the present invention, the solvent used in step (i) is selected from methylene chloride, acetone, water and the like or mixtures thereof.

In an embodiment of the present invention, the alkali iodide used in step (i) is selected from sodium iodide, lithium iodide or potassium iodide.

In an embodiment of the present invention, the reaction with acetaldehyde in step (ii) is carried out using solvents such as DMF, isopropyl alcohol, methylene chloride, acetone, acetonitrile and the like or mixtures thereof.

In an embodiment of the present invention, the reaction with acetaldehyde in step (ii) is carried out preferably at a temperature in the range of 0–5° C.

In yet another embodiment of the present invention, the deesterification in step (iii) is carried out using phenol, phenol/trifluoroacetic acid, anisole/trifluoroacetic acid, formic acid using solvent such as methylene chloride, ethyl acetate, water and the like or mixtures thereof.

In yet another embodiment of the present invention, the conversion in step (iv) is carried out in the presence of solvent selected from water, acetone, DMF, THF, DMAc, DMSO, halogenated alkanes like methylene chloride, ethylene chloride, $CCl_4$, $CHCl_3$ and the like or mixtures thereof using base such as inorganic base like sodium hydroxide, lithium hydroxide, potassium hydroxide, ammonium hydroxide or organic base such as tertiary butyl amine, benzyl amine, dibenzyl amine, diethyl amine, triethyl amine, dicyclohexyl amine, cyclohexyl amine, benzothiazole and the like.

In an embodiment of the present invention, the neutralization in step (v) is carried out using solvents such as ethyl acetate, water and like or mixture thereof.

In an embodiment of the present invention, the neutralization in step (v) is carried out using ammonia.

In an embodiment of the present invention, the enzymatic hydrolysis in step (v) is carried out using PenG-amidase.

In yet another embodiment of the present invention, the silylation in step (vi) is carried out in the presence of halogenated solvents such as methylene chloride, ethylene chloride, $CCl_4$, $CHCl_3$ and the like.

In yet another embodiment of the present invention, the condensation in step (vii) is carried out in the presence of halogenated solvents such as methylene chloride, ethylene chloride, $CCl_4$, $CHCl_3$ and the like and base such as triethylamine, N-methyl morpholine, diethylamine and the like.

In another embodiment of the present invention, there is provided a process for the preparation of cefprozil of the formula (XIV)

(XIV)

from cefprozil DMF solvate of the formula (I) by known methods.

In yet another embodiment of the present invention, the mixed anhydride of the formula (XIII) is prepared from Dane salt of formula (XV)

(XV)

wherein $R_3$ represents methyl, ethyl or isopropyl and $Y^+$ is sodium or potassium and chloroformate of formula (XVI)

(XVI)

wherein $R_2$ represents alkyl, phenyl, benzyl or cycloalkyl in the presence of solvents selected from mixtures of methylene chloride/dimethyl acetamide, ethylene chloride/dimethyl acetamide, methylene chloride/DMF, ethylene chloride/DMF and the like and catalysts such as N-methyl morpholine.

In yet another embodiment of the present invention, there is provided an intermediate of formula (XI)

(XI)

wherein $M^+$ represents a counter ion which forms a salt.

In yet another embodiment of the present invention, the counter ion represented by $M^+$ is selected from sodium, potassium, lithium, ammonium tertiary butyl ammonium, benzyl ammonium, dibenzyl ammonium, diethyl ammonium, triethyl ammonium, dicyclohexyl ammonium, benzothiazole and the like.

The compound of formula (XI) obtained is enriched in (Z) isomer. Using this compound as an intermediate for the preparation of compound of formula (I), we could achieve the preparation of compound of formula (I) with enriched (Z) isomer.

The advantage of using the combination of HMDS and trimethyl silyl chloride as a silylating agent is that the reaction is faster and the formation of impurities is less.

The present invention is provided by the examples given below, which are provided by way of illustration only and should not be considered to limit the scope of the invention.

EXAMPLE 1

Step (i)

Preparation of 4-methoxybenzyl 7-phenylacetamido-3-[(triphenylphosporanylidene) methyl]-3-cephem-4-carboxylate (VIII) To a suspension of 4-methoxybenzyl 7-phenylacetamido-3-chloromethyl-3-cephem-4-carboxylate (VII) (100 g, 0.2053 mol) in methylene chloride (600 ml), NaI (32.3 g, 0.2155 mol), triphenylphosphine (56.6 g, 0.2157 mol) and water (600 ml) were added. The mixture was stirred at 32 to 35° C. under nitrogen atmosphere for 90 min. The organic layer was separated and IN NaOH (217 ml) was added. The resulting reddish brown mixture was stirred at 30 to 32° C. for 20 min. The organic layer was separated and washed with water (500 ml) followed by 20% w/w aq. NaCl solution (500 ml). The organic layer was diluted upto 1000 ml using fresh methylene chloride. The title compound (VIII) in methylene chloride used as such in the next reaction.

Step (ii)

Preparation of 4-methoxybenzyl 7-phenylacetamido-3-[(Z/E)-propen-1y1]-3-cephem-4-carboxylate (IX)

To a cold suspension of lithium chloride (26.2 g, 0.618 mol) in dry DMF (100 ml), the solution of 4-methoxybenzyl 7-phenylacetamido-3-[(triphenylphosporanylidene)methyl]-3-cephem-4-carboxylate (VIII) obtained in step (i) in methylene chloride (1000 ml) was added. The resulting solution was cooled to 0 to 5° C. Acetaldehyde (139 ml, 2.46 mol) was added to the above mixture at 0 to 5° C. The reaction mixture was stirred for 18 hrs at 0 to 5° C. and water (400 ml) was added and stirred at 10 to 15° C. for 10 min. The organic layer was separated, concentrated under vacuum and washed. To this concentrate, IPA (800 ml) was added at 30° C. and stirred to get the precipitate of (IX). Water (900 ml) was added and filtered to yield the title compound (yield 86 g, purity 92.6%, Z/E ratio 92.4/7.5, by HPLC).

Step (iii)

Preparation of 7-phenylacetamido-3-[(Z/E)-propen-1-yl]-3-cephem-4-carboxylic acid (X) 4-Methoxybenzyl 7-phenylacetamido-3-[(Z/E)-propen-1-yl]-3-cephem-4-carboxylate obtained in step (ii) (50 g) was dissolved in phenol (50 ml) and trifluoroacetic acid (TFA) (14.5 g). The reaction mixture was stirred at 30 to 35° C. for 4 to 5 hrs and transferred to a mixture of water (250 ml) and ethyl acetate (250 ml) at 20° C. The pH was adjusted to 8.0 using 2N NaOH solution. The organic layer was separated and aq.layer was extracted with ethyl acetate (50 ml). The combined aq.layer was charcoalised and filtered. pH of the filtrate was adjusted to 2.0 to 2.5 with 15% sulfuric acid and stirred for 30 min. Filtered and washed with water (2×50 ml) to yield the title compound (yield (wet) 74 g, purity 97.6%, Z/B ratio 90.0/10.0, by HPLC).

Step (iv)

Preparation of 7-phenylacetamido-3-[(Z/E)-propen-1-yl]-3-cephem-4-carboxylic acid dicyclohexylamine salt (XI) 7-Phenylacetamido-3-[(Z/E)-propen-1-yl]-3-cephem-4-carboxylic acid obtained in step (iii) above (5 g) dissolved in acetone (80 ml) and water (40 ml). To this solution dicyclohexylamine (2.5 g) was added, stirred and filtered through suction and washed with ethyl acetate (10 ml) to yield the title compound (yield 2.5 g, purity 99.6%, Z/E ratio 93.7/6.3, by HPLC).

Step (v)

Preparation of 7-amino-3-[(Z/E)-propen-1-yl]-3-cephem-4-carboxylic acid (V) 7-Phenylacetamido-3-[(Z/E)-propen-1-yl]-3-cephem-4-carboxylic acid dicyclohexylamine salt (100 g) prepared according to the process described in step (iv) was taken in ethyl acetate (1.6 lt) and water (1.0 lt). pH of resulted slurry was adjusted to 2.0 using 15% sulfuric acid. The layers were separated. To the ethyl acetate layer, water (1.0 lt) was added and pH was adjusted to 8.0 using 10% ammonia solution. The layers were separated and the aqueous layer was washed with butyl acetate (250 ml). To the aqueous layer, PenG-amidase (48 g, dry basis) was added. pH was maintained between 7.8 and 8.0 using 5% ammonia for 4 to 5 hrs. PenG-amidase was separated by filtration and the filtrate was treated with activated carbon. Carbon was filtered off and pH of the filtrate was adjusted to 3.5 using 1:1 HCl solution at 30° C. The precipitate was stirred, filtered and washed with water (2×60 ml) and dried to yield the title compound (yield 39 g, purity 99.2%, Z/E ratio 92.3/7.7).

Step (vi)

Preparation of (6R,7R)-7-[2-amino-2-(4-hydroxyphenyl)acetamido]-3-[(Z)-propenyl]-3-cephem-4-carboxylic acid DMF solvate (I) 7-Amino-3-[(Z/E)-propen-1-yl]-3-cephem-4-carboxylic acid (V) (50 g. 0.2081 mol) prepared according to the process described in step (v) was stirred in methylene chloride (250 ml) at 30° C. Trimethylsilylchloride (17.3 g, 0.1594 mol) and hexamethyldisilazane (25.75 g, 0.1594 mol) were added and stirred for 2 hrs at 30 to 35° C. to form compound (XII) in situ. Then cooled to −10° C.

Simultaneously, p-hydroxy phenyl glycine Dane salt (67.4 g, 0.2223 mol) in methylene chloride (350 ml) was stirred and cooled to −10° C. DMF (120 ml) was added and further cooled to −45° C. N-methylmorpholine (0.5 ml) and ethylchloroformate (24.8 g, 0.2285 mol) were added and stirred for 1.5 hrs at −40° C. to −45° C. to form compound (XIII).

The cold mixture of compound (XII) was added into compound (XIII) at −60° C. The resulting slurry was stirred at −45° C. to −50° C. for 1.5 hrs. 1:1 HCl (55 ml) and water (100 ml) were added at −45° C. The temperature was gradually allowed to raise to 5° C. and stirred for 10 min.

The aq. layer was separated, the organic layer was extracted with 1:1 HCl solution (10 ml) and the combined aq. layers were cooled to 0 to 5° C. DMF (600 ml) and IPA (300 ml) were added and stirred at 0 to 5° C. for 10 min. and filtered. The filtrate was warmed to 30° C., triethylamine was added rapidly to adjust the pH to 6 at 30 to 35° C. The slurry was stirred at 0 to 5° C. for 1 hr. The precipitate was filtered and washed with IPA (80 ml) followed by acetone (300 ml). The wet material was air dried to yield the title compound (yield 110.4 g, purity 97.69, moisture content 3.4%, Z/E ratio 92.3/7.7).

Step (vii)

Preparation of (6R,7R)-7-[2-amino-2-(4-hydroxyphenyl)acetamido]-3-[(Z)-propenyl]-3-cephem-4-carboxylic acid monohydrate (XIV) (6R,7R)-7-[2-Amino-2-(4-hydroxyphenyl)acetamido]-3-[(Z)-propenyl]-3-cephem4-carboxylic acid DMF solvate (I) (110 g) was stirred in water (160 ml) at 30° C. for 40 min. The crude compound was collected by filtration and washed with water (30 ml) followed by acetone (30 ml). The wet crude was dried in vacuum at room temperature to give dried material which was then stirred in water (140 ml) at 150° C., pH was adjusted to 1.0 using 1:1 HCl to get clear solution. Then pH was readjusted to 5.0 using 10% ammonia solution at 15 to 20° C. The precipitate was cooled to 2 to 5° C., stirred for 1.5 hr, filtered and washed with water (30 ml) followed by acetone (30 ml) and dried in vacuum at room temperature to give the title compound (yield 65 g, 98.96% pure, moisture content 5.5%, Z/E ratio 91.5/8.5).

EXAMPLE 2

Step (i)

Preparation of 4-methoxybenzyl 7-phenylacetamido-3-[(triphenylphosporanylidene)methyl]-3-cephem-4-carboxylate (VIII)

To a stirred suspension of 4-methoxybenzyl 7-phenylacetamido-3-chloromethyl-3-cephem-4-carboxylate (VII) (10 g, 0.0205 mol) in acetone (50 ml), sodium iodide (3.1 g, 0.0207 mol) and triphenylphosphine (5.9 g, 0.0226 mol) were added. The mixture was stirred at 30 to 32° C. for 1.5 hrs. The resulting mixture was concentrated in vacuo to get the residual oil. To this concentrate methylene chloride (50 ml) was added and to the resultant solution, 2N NaOH solution (20 ml) was added and stirred at 30 to 32° C. for 20 min. The organic layer was separated and washed with water (25 ml) and dried over anhydrous sodium sulfate to give the title compound (VIII) in methylene chloride.

Step (ii)

Preparation of 4-methoxybenzyl 7-phenylacetamido-3-[(Z/E)-propen-1-yl]-3-cephem-4-carboxylate (IX)

To a cold suspension of lithium chloride (26.2 g, 0.6179 mol) in dry DMF (100 ml), the solution of 4-methoxybenzyl 7-phenylacetamido-3-[(triphenylphosporanylidene)methyl]-3-cephem-4-carboxylate (VIII) obtained according to the process described in step (i) in methylene chloride (1000 ml) was added. The resulting solution was cooled to 0 to 5° C. Acetaldehyde (139 ml, 2.48 mol) was added to the above mixture at 0 to 5° C. The reaction mixture was stirred for 18 hrs at 0 to 5° C. and water (400 ml) was added and stirred at 10 to 15° C. for 10 min. The organic layer was separated, concentrated under vacuum and washed. To this concentrate, IPA (800 ml) was added at 30° C. and stirred to get the precipitate of (IX). Water (900 ml) was added and filtered to yield the title compound (yield 86 g, purity 93%, Z/E ratio 92.2/7.8).

Step (iii)

Preparation of 7-phenylacetamido-3-[(Z/E)-propen-1-yl]-3-cephem-4-carboxylic acid dicyclohexylamine salt (XI)

Methoxybenzyl 7-phenylacetamido-3-[(Z/E)-propen-1-yl]-3-cephem-4-carboxylate obtained in step (ii) above (50 g) was dissolved in phenol (50 ml) and TFA (14.25 g) and it was stirred at 30 to 35° C. for 3 to 4 hrs. The mixture was added to cold mixture of water (250 ml) and ethyl acetate (250 ml), pH was adjusted to 8.0 using 2N NaOH solution at 20–22° C. The aq. layer was separated and ethyl acetate (400 ml) was added and the pH was adjusted to 2.0 to 2.3 using 15% w/v sulfuric acid. The upper ethyl acetate layer was separated and to this water (300 ml) and acetone (50 ml) were added. Dicyclohexylamine was added in drops and pH adjusted to 5.0. Subsequently the resultant precipitate was stirred, filtered, washed with ethyl acetate (50 ml) and dried to give the title compound (yield (dry) 35 g, purity 99.6%, Z/E ratio 94.6/5.4).

Step (iv)
Preparation of 7-amino-3-[(Z/E)-propen-1-yl]-3-cephem-4-carboxylic acid (V) 7-Phenylacetamido-3-[(Z/E)-propen-1-yl]-3-cephem-4-carboxylic acid dicyclohexylamine salt (100 g) prepared according to the process described in step (iii) was taken in ethyl acetate (1.6 lt) and water (1.0 lt). pH of resulted slurry was adjusted to 2.0 using 15% sulfuric acid. The layers were separated. To the ethyl acetate layer, water (1.0 lt) was added and pH was adjusted to 8.0 using 10% ammonia solution. The layers were separated and the aqueous layer was washed with butyl acetate (250 ml). To the aqueous layer, PenG-amidase (48 g. dry basis) was added. pH was maintained between 7.8 and 8.0 using 5% ammonia for 4 to 5 hrs. PenG-amidase was separated by filtration and filtrate was treated with activated carbon. Carbon was filtered off and pH of the filtrate was adjusted to 3.5 using 1:1 HCl solution at 30° C. The precipitate was stirred, filtered and washed with water (2×60 ml) and dried to yield the title compound (yield 39 g, purity 98.2%, Z/E ratio 93.6/6.4).

Step (v)
Preparation of (6R,7R)-7-[2-amino-2-(4-hydroxyphenyl)acetamido]-3-[(Z)propenyl]-3-cephem-4-carboxylic acid DMF solvate (I) 7-Amino-3-[(Z/E)-propen-1-yl]-3-cephem-4-carboxylic acid (V) (50 g, 0.2081 mol) prepared according to the process described in step (iv) was stirred in methylene chloride (250 ml) at 30° C. Trimethylsilylchloride (17.3 g. 0.1594 mol) and hexamethyldisilazane (25.75 g, 0.1594 mol) were added and stirred for 2 hrs at 30 to 35° C. to form compound (XII) in situ. Then cooled to –10° C.

Simultaneously, p-hydroxy phenyl glycine Dane salt (67.4 g, 0.2223 mol) in methylene chloride (350 ml) was stirred and cooled to –10° C. DMF (120 ml) was added and further cooled to –45° C. N-methylmorpholine (0.5 ml) and methylchloroformate (21.59 g, 0.2285 mol) were added and stirred for 1.5 hrs at –40° C. to –45° C. to form compound (XIII).

The cold mixture of compound (XII) was added into compound (XIII) at –60° C. The resulting slurry was stirred at –45° C. to –50° C. for 1.5 hrs. 1:1 HCl (55 ml) and water (100 ml) were added at –45° C. The temperature was gradually allowed to raise to 5° C. and stirred for 10 min. The aq. layer was separated, the organic layer was extracted with 1:1 HCl solution (10 ml) and the combined aq. layers were cooled to 0 to 5° C. DMF (600 ml) and IPA (300 ml) were added and stirred at 0 to 5° C. for 10 min. and filtered. The filtrate was warmed to 30° C., triethylamine was added rapidly to adjust the pH to 6 at 30 to 35° C. The slurry was stirred at 0 to 5° C. for 1 hr. The precipitate was filtered and washed with IPA (80 ml) followed by acetone (300 ml). The wet material was air dried to yield the title compound (yield 110.4 g, moisture content 3.4%, purity 97.4%, Z/E ratio 91.8/8.2).

Step (vi)
Preparation of (6R,7R)-7-[2-amino-2-(4-hydroxyphenyl)acetamido]-3-[(Z)-propenyl]-3-cephem-4-carboxylic acid monohydrate (XIV) (6R,7R)-7-[2-Amino-2-(4-hydroxyphenyl)acetamido]-3-[(Z)-propenyl]-3-cephem-4-carboxylic acid DMF solvate (I) (110 g) was stirred in water (160 ml) at 30° C. for 40 min. The crude compound was collected by filtration and washed with water (30 ml) followed by acetone (30 ml). The wet crude was dried in vacuum at room temperature to give dried material which was then stirred in water (1 40 ml) at 15° C., pH was adjusted to 1.0 using 1:1 HCl to get clear solution. Then pH was readjusted to 5.0 using 10% ammonia solution at 15 to 20° C. The precipitate was cooled to 2 to 5° C., stirred for 1.5 hr, filtered and washed with water (30 ml) followed by acetone (30 ml) and dried in vacuum at room temperature to give the title compound (yield 65 g, moisture content 5.5%, purity 98.45%, Z/E ratio 91.3/8.7).

EXAMPLE 3

Step (i)
Preparation of 4-methoxybenzyl 7-phenylacetamido-3-[(triphenylphosporanylidene) methyl]-3-cephem-4-carboxylate (VIII)
To a suspension of 4-methoxybenzyl 7-phenylacetamido-3-chloromethyl-3-cephem-4-carboxylate (VII) (100 g, 0.2053 mol) in methylene chloride (600 ml), NaI (32.3 g, 0.2155 mol), triphenylphosphine (56.6 g, 0.2155 mol) and water (600 ml) were added. The mixture was stirred at 32 to 35° C. under nitrogen atmosphere for 90 min. The organic layer was separated and 1N NaOH (217 ml) was added. The resulting reddish brown mixture was stirred at 30 to 32° C. for 20 min. The organic layer was separated and washed with water (500 ml) followed by 20% w/w aq. NaCl solution (500 ml). The organic layer was diluted upto 1000 ml using fresh methylene chloride. The title compound (VIII) in methylene chloride used as such in the next reaction.

Step (ii)
Preparation of 4-methoxybenzyl 7-phenylacetamido-3-[(Z/E)-propen-1-yl]-3-cephem-4-carboxylate (IX)
To a cold solution of 4-methoxybenzyl 7-phenylacetamido-3-[(triphenylphosporanylidene)methyl]-3-cephem-4-carboxylate (VIII) obtained in step (i) above in methylene chloride (500 ml) lithium chloride (13.1 g, 0.3089 mole) and dry DMF (50 ml) were added. The resulting solution was cooled to 0 to 5° C. Acetaldehyde (69.5 ml, 1.24 mole) was added to the above mixture at 0 to 5° C. The reaction mixture was stirred for 18 hrs at 0 to 5° C. and water (200 ml) was added and stirred at 10 to 15° C. for 10 min. The organic layer was separated, concentrated under vacuum and washed. To this concentrate, IPA (400 ml) was added at 30° C. and stirred to get the precipitate of (IX). Water (450 ml) was added and filtered to yield the title compound (yield 44.6 g, purity 93.7%, Z/E ratio 92.2/7.8).

Step (iii)
Preparation of 7-phenylacetamido-3-[(Z/E)-propen-1-yl]-3-cephem-4-carboxylic acid cyclohexylamine salt (XI) 4-Methoxybenzyl 7-phenylacetamido-3-[(Z/E)-propen-1-yl]-3-cephem-4-carboxylate obtained in step (ii) above (20 g) was dissolved in phenol (20 ml) and TFA (5.7 g) and it was stirred at 30 to 35° C. for 3 to 4 hrs. The mixture was added to cold mixture of water (100 ml) and ethylacetate (100 ml), pH was adjusted to 8.0 using 2N NaOH solution at 20–22° C. The aq. layer was separated and ethylacetate (140 ml) was added and the pH was adjusted to 2.0 to 2.3 using 15%w/v sulfuric acid. The upper ethyl acetate layer was separated and to this water (25 ml) and acetone (50 ml) were added. Cyclohexylamine was added in drops and pH adjusted to 5.5. Subsequently the resultant precipitate was stirred, filtered, washed with ethylacetate (20 ml) and dried to give the title compound (yield (dry) 8.2 g, purity 99.68%, Z/E ratio 93.1/ 6.9).

Step (iv)

Preparation of 7-amino-3-[(Z/E)-propen-1-yl]-3-cephem-4-carboxylic acid (V) 7-Phenylacetamido-3-[(Z/E)-propen-1-yl]-3-ceph-em-4-carboxylic acid cyclohexylamine salt (100 g) prepared according to the process described in step (iii) was taken in ethyl acetate (1 .6 lt) and water (1.0 lt). pH of resulted slurry was adjusted to 2.0 using 15% sulfuric acid. The layers were separated. To the ethyl acetate layer, water (1.0 lt) was added and pH was adjusted to 8.0 using 10% ammonia solution. The layers were separated. The aqueous layer was washed with butyl acetate (250 ml). To the aqueous layer, PenG-amidase (48 g, dry basis) was added. pH was maintained between 7.8 and 8.0 using 5% ammonia for 4 to 5 hrs. PenG-amidase was separated by filtration and the filtrate was treated with activated carbon. Carbon was filtered off and pH of the filtrate was adjusted to 3.5 using 1:1 HCl solution at 30° C. The precipitate was stirred, filtered and washed with water (2×60 ml) and dried to yield the title compound (yield 39 g).

Step (v)

Preparation of (6R,7R)-7-[2-amino-2-(4-hydroxyphenyl) acetamido]-3-[(Z)-propenyl]-3-cephem-4-carboxylic acid DMF solvate (I) 7-Amino-3-[(Z/E)-propen-1-yl]-3-cephem-4-carboxylic acid (V) (50 g, 0.2081 mol) was stirred in methylene chloride (250 ml) at 30° C. Trimethylsilylchloride (17.3 g, 0.1594 mol) and hexamethyldisilazane (25.75 g, 0.1594 mol) were added and stirred for 2 hrs at 30 to 35° C. to form compound (XII) in situ. Then cooled to −10° C.

Simultaneously, p-hydroxy phenyl glycine Dane salt (67.4 g, 0.2223 mol) in methylene chloride (350 ml) was stirred and cooled to −10° C. DMF (120 ml) was added and further cooled to −45° C. N-methylmorpholine (0.5 ml) and ethylchloroformate (24.8 g, 0.2285 mol) were added and stirred for 1.5 hrs at −40° C. to −45° C. to form compound (XIII).

The cold mixture of compound (XII) was added into compound (XIII) at −60° C. The resulting slurry was stirred at −45° C. to −50° C. for 1.5 hrs. 1:1 HCl (55 ml) and water (100 ml) were added at −45° C. The temperature was gradually allowed to raise to 5° C. and stirred for 10 min. The aq. layer was separated, the organic layer was extracted with 1:1 HCl solution (10 ml) and the combined aq. layers were cooled to 0 to 5° C. DMF (600 ml) and IPA (300 ml) were added and stirred at 0 to 5° C. for 10 min. and filtered. The filtrate was warmed to 30° C., triethylamine was added rapidly to adjust the pH to 6 at 30 to 35° C. The slurry was stirred at 0 to 5° C. for 1 hr. The precipitate was filtered and washed with IPA (80 ml) followed by acetone (300 ml). The wet material was air dried to yield the title compound (yield 110.4 g, moisture content 3.4%).

Step (vi)

Preparation of (6R,7R)-7-[2-amino-2-(4-hydroxyphenyl) acetamido]-3-[(Z)-propenyl]-3-cephem-4-carboxylic acid monohydrate (XIV) (6R,7R)-7-[2-Amino-2-(4-hydroxyphenyl)acetamido]-3-[(Z)-propenyl]-3-cephem-4-carboxylic acid DMF solvate (I) (110 g) was stirred in water (160 ml) at 30° C. for 40 min. The crude compound was collected by filtration and washed with water (30 ml) followed by acetone (30 ml). The wet crude was dried in vacuum at room temp to give dried material which was then stirred in water (140 ml) at 15° C., pH was adjusted to 1.0 using 1:1 HCl to get clear solution. Then pH was readjusted to 5.0 using 10% ammonia solution at 15 to 20° C. The precipitate was cooled to 2 to 5° C., stirred for 1.5 hr, filtered and washed with water (30 ml) followed by acetone (30 ml) and dried in vacuum at room temperature to give the title compound (yield 65 g, 99.1% pure, moisture content 5.5%).

What is claimed is:

1. An improved process for the preparation of cefprozil DMF solvate of formula (I)

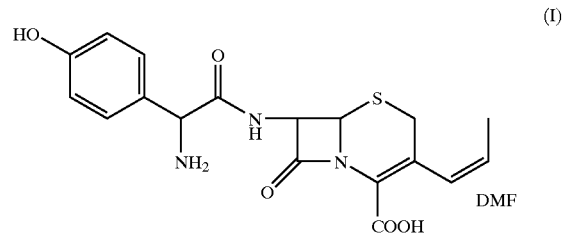

comprising the steps of:

i) reacting the compound of formula (VIII)

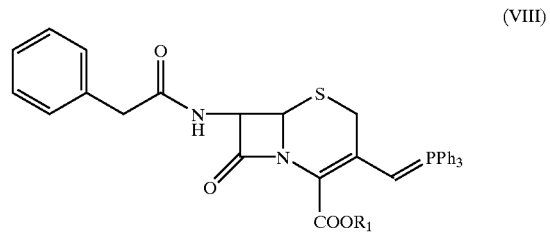

with acetaldehyde using lithium chloride in the presence of a solvent at a temperature in the range of −10° C. to 30° C. to produce a compound of formula (IX)

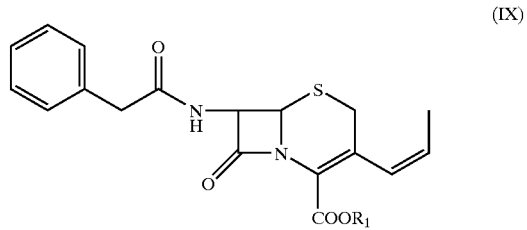

wherein $R_1$ represents a carboxy protecting group, ii) deesterifying the carboxy protecting group of the compound of formula (IX) using an acid in the presence of a solvent at a temperature in the range of 10° C. to 50° C. to yield a compound of formula (X),

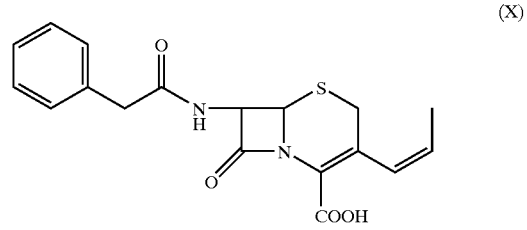

iii) converting the compound of formula (X) to a compound of formula (XI)

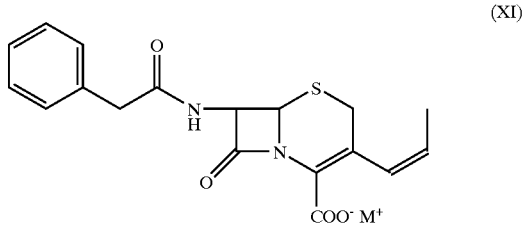

(XI)

wherein M⁺ represents a counter ion which forms a salt in the presence of a base and solvent, iv) neutralizing the compound of formula (XI) followed by enzymatic hydrolysis using conventional methods to produce the APCA of formula (V),

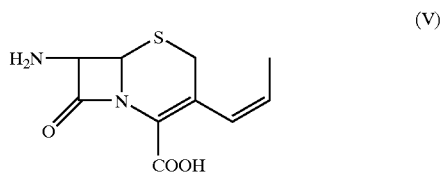

(V)

v) silylating the APCA of formula (V) using a mixture of trimethyl silylchloride and hexamethyl disilazane in the presence of a halogenated solvent to produce silylated APCA of formula (XII) and

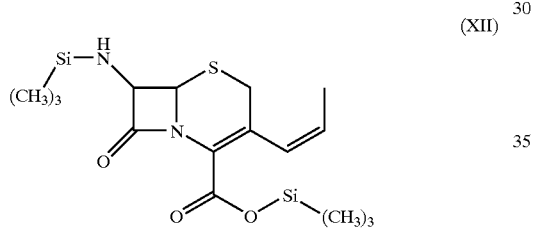

(XII)

vi) condensing the silylated APCA of formula (XII) with the mixed anhydride of formula (XIII)

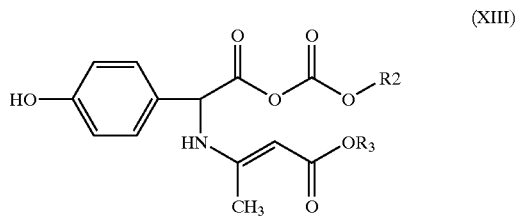

(XIII)

wherein $R_2$ represents alkyl, phenyl, benzyl or cycloalkyl and $R_3$ represents methyl, ethyl or isopropyl, in the presence of DMF, a halogenated solvent and a base at a temperature in the range of −50° C. to 10° C. to produce cefprozil DMF solvate of formula (I).

2. The process as claimed in claim 1, wherein the carboxy protecting group represented by $R_1$ is methyl, ethyl, propyl, isopropyl, p-methoxybenzyl, p-nitrobenzyl, o-chlorobenzyl, or diphenylmethyl.

3. The process as claimed in claim 1, wherein the solvent used for the reaction with acetaldehyde in step (i) is DMF, isopropyl alcohol, methylene chloride, acetonitrile or mixtures thereof.

4. The process as claimed in claim 1, wherein the solvent used for deesterification in step (ii) is methylene chloride, ethyl acetate, water or mixtures thereof.

5. The process as claimed in claim 1, wherein the deesterification in step (ii) is carried out using phenol/trifluoroacetic acid, anisole/trifluoroacetic acid, formic acid using a solvent selected from the group consisting of methylene chloride, ethyl acetate, and water, or mixtures thereof.

6. The process as claimed in claim 1, wherein the solvent used in step (iii) is water, acetone, DMF, THF, DMAc, DMSO, halogenated alkane or mixtures thereof.

7. The process as claimed in claim 1, wherein the base used in step (iii) is sodium hydroxide, lithium hydroxide, potassium hydroxide, ammonium hydroxide or an organic base selected from the group consisting of tertiary butyl amine, benzyl amine, dibenzyl amine, triethyl amine, diethyl amine, dicyclohexyl amine, cyclohexyl amine and benzothiazole.

8. The process as claimed in claim 1, wherein the halogenated solvent used in step (v) is methylene chloride, ethylene chloride, $CCl_4$ or $CHCl_3$.

9. The process as claimed in claim 1, wherein the base used in step (vi) is triethylamine, N-methyl morpholine or diethylamine.

10. An intermediate of formula (XI)

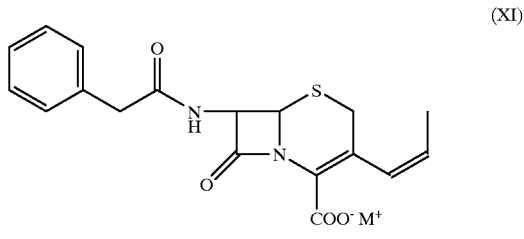

(XI)

wherein M⁺ represents a counter ion which forms a salt selected from the group consisting of sodium, lithium, potassium, ammonium, tertiary butyl ammonium, benzyl ammonium, dibenzyl ammonium, diethyl ammonium, triethyl ammonium, dicyclohexyl ammonium, cyclohexyl ammonium and benzothiazolium.

11. The process as claimed in claim 1, further comprising converting the compound of formula (I) into cefprozil of formula (XIV).

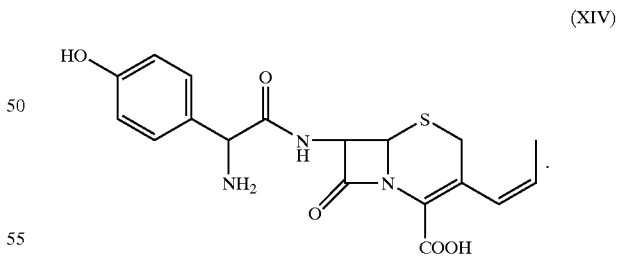

(XIV)

12. The process as claimed in claim 6, wherein the halogenated alkane is selected from the group consisting of methylene chloride, ethylene chloride, $CCl_4$, $CHCl_3$ and mixtures thereof.

* * * * *